United States Patent [19]

Kinoshita et al.

[11] 4,293,226
[45] Oct. 6, 1981

[54] PHOTOGRAPHIC FILM BLACKENING AREA MEASURING DEVICE

[75] Inventors: Minoru Kinoshita, Kyoto; Kiyoshi Sugou, Yokohama; Yukio Onoda, Kusatsu, all of Japan

[73] Assignee: Dainippon Screen Seizo Kabushiki Kaisha, Kyoto, Japan

[21] Appl. No.: 151,400

[22] Filed: May 19, 1980

[30] Foreign Application Priority Data

Jun. 21, 1979 [JP] Japan .............................. 54-85762[U]

[51] Int. Cl.$^3$ ........................ G01N 21/59; G02B 5/14
[52] U.S. Cl. ..................................... 356/443; 250/227
[58] Field of Search ............... 356/432, 439, 443, 444, 356/380; 250/227; 350/96.1, 96.15, 96.16, 96.2

[56] References Cited

U.S. PATENT DOCUMENTS 3,317,738  5/1967  Piepenbrink et al. ............... 250/227
3,617,132  11/1971  Bell ..................................... 356/432

Primary Examiner—John K. Corbin
Assistant Examiner—Bruce Y. Arnold
Attorney, Agent, or Firm—Zarley, McKee, Thomte, Voorhees & Sease

[57] ABSTRACT

A photographic film blackened area measuring device, having two rod shaped light conducting members, each of which is formed as an elongated piece of transparent material with part of its surface, parallel to its axis, being roughened so as to diffuse light, while light is totally internally reflected along the length of the rod shaped member from the remainder of its smooth surface. These rod shaped light conducting members are arranged one on each side of a piece of developed photographic film in a automatic film developing machine, and the film passes between them. A light emitting device is provided at one end of one of the rod shaped light conducting members, and a photo sensitive device is provided at the end of the other rod shaped light conducting member which is remote from the light emitting device. Thereby, as the photographic film moves between the rods, fluctuations of the output of the light sensitive device are produced, depending on the total area of blackening of the photographic film, but substantially independent of the positioning and arrangement of said blackened area with respect to the edges of the film.

5 Claims, 4 Drawing Figures

PHOTOGRAPHIC FILM BLACKENING AREA MEASURING DEVICE

BACKGROUND OF THE INVENTION

The present invention relates to the field of automatic photographic film development, which is applicable to realization of automatic control of replenishment of photographic film developing solution by automatic detection of the total blackening area of a photographic film which has been processed in the solution.

Recently, in the field of automatic photomechanical film processing, machines have come into widespread commercial use for development of photographic film. During the operation of such an automatic photographic film development machine, photographic film which has been exposed is transported, by an appropriate transfer system, through a plurality of film processing tanks containing liquid, such as, for example, one or more film developing tanks containing developer, a washing tank, a fixing tank containing fixing solution, and a drying tank. Various such devices are well known to those skilled in the art as means for performing the necessary film developing and processing. Problems are liable to occur with such automatic photographic film developing machines with regard to streaking and uneven development of the finished photographic films. In particular, such streaking and/or uneven development can often be caused by fatigue of certain reacting chemicals in the developer contained in the film developing tank or tanks. Therefore it has become well known, and practiced, to effect replenishment and/or changing of the developer in the film developing tank. In other words, as the processing of photographic film continues, the photographic film which is being developed absorbs chemicals from the developer and releases chemicals into the developer, and thereby the developer becomes both exhausted and also contaminated, and, therefore, replenishment and/or replacement of the developer in order to restore its developing effectiveness is carried out by adding a suitable amount of extra developer and/or draining a part or all of the exhausted and contaminated developer.

It is clear that the operation of replenishment of such a developer solution must be carefully controlled. That is to say, the amount of added solution must be carefully regulated. If too little developer solution is added to the exhausted or contaminated developer in the developing tank, the problems of streaking of the photographic film and uneven development thereof will not be obviated. On the other hand, if too much additional developing solution is added to the exhausted and contaminated developer solution in the developing tank, the problem may arise, especially in the development of litho film for printing, that the contrast of the final image on the photographic film may be reduced. Further, additional cost is incurred. Both of these results are undesirable, and therefore good control of addition of developer is essential.

A means must therefore be provided to effect this control reliably and effectively. Various means have in the past been suggested for performing this control. In principle, the amount of exhaustion and contamination of the developer is approximately proportional to the total area of blackening produced in the photographic film that has been developed in that solution. That is to say, passing of unexposed photographic film through the developer, substantially, does not greatly affect the properties of the developer; on the other hand, development of exposed photographic film by the developer entails the substantial reaction of the developer with chemicals in the film, and thus entails contamination of and exhaustion of the developer. Therefore it has been conceived, and practiced, to sense the ongoing area of blackening of photographic film as it is processed through the developer, and to total this blackening area, and from time to time to replenish and/or replace the developer, based upon calculation of the total area of blackening produced in the photographic film by the solution which is currently in the developing tank.

For this purpose, various automatic film development machines have already been produced which detect photoelectrically the area of blackening produced on photographic film which has been processed by the machine, and, based upon this detected film blackening area, which perform the control of replenishment and/or replacing of developer. Such machines for automatic film development use photoelectric detection mechanisms provided in a certain place in the film transport path of the photographic film, after it has passed through the developer—typically, between the film washing tank and the film drying tank—and, based upon the total ongoing moment by moment film blackening area detected by this photoelectric detecting device, the total area of blackening of the entire photographic film which has passed through the developer currently in the developing tank is calculated. Based upon this calculated value, a decision is made from time to time as to whether, and when, to replenish and/or replace the developer in the developing tank. This is done on the basis of data that have been previously determined by the process of experiment. Thus, the required amount of replenishing developer is added to the developing tank.

In the construction and operation of such a device, it is essential that the response of such a photoelectric detecting device should be uniform with respect to distance across the width of the film which is moving past it. That is to say, the effect on the photoelectric detecting device produced by one unit of blackening of the film should be the same, wherever the blackened part of film is located with respect to the width of the film. This is because the position of blackened portions of the film on the film surface will change, perhaps in a systematic manner, according to the pattern of the photographs that are being developed on the photographic film. For example, in some cases the photographs which are being developed on the photographic film may all have a blackened area towards the centre of the photographic film, and may all have lighter areas towards the edges of the film; whereas, on the other hand, it is possible that the pictures which are being developed may all have blackened areas towards the edges of the photographic film, and lightened areas towards the centre of the film. Of course, the amount of replenishing fluid required for the developing solution is completely unrelated to the actual positions of the images which have been developed on the photographic film, and, on the other hand, only depends upon the total blackened area of the film, or, more precisely, on the amount of blackening of each point of the surface of the film, integrated over the total surface area of the film that has been developed in the developer currently in the developing tank. Thus, for a particular total area of blackening of film to a particular degree, a particular amount of replenishing developer is required, irrespective of the actual positioning of this blackening over the area of the film that has been developed.

For this uniform measuring of area of blackening of the film over its surface area, therefore, it is required to install a blackened area detecting device which extends across the width of the film, and whose response to blackening of the film is uniform across the width of the film. Therefore, it has been proposed, in the prior art, to construct such a photoelectric film blackened area measuring device by arranging a plurality of light sources in a straight line across the film, the film being transported past these light sources, and to arrange a plurality of light detectors such as photoelectric cells, again arranged in a straight line, on the other side of the film from the light sources. Thereby, the light from the light sources illuminates the film, over its width, effectively uniformly, and the light detectors, whose response, again, is uniform over the width of the film, pick up signals whose intensity corresponds to the area of blackening of the photographic film.

Further, as an alternative possibility, it has been proposed and practiced in the prior art to provide this plurality of light sources, not as independent light sources, but as ends of a bundle of optical fibers. These ends are disposed along a line reaching across the width of the film, and the other ends of these optical fibers are gathered together and juxtaposed to a single light source. Similarly, on the other side of the film, the light detectors are arranged as being the ends of a bundle of light fibers, said ends being arranged along a line parallel to the light emitting ends of the first light fibers, and on the other side of the film therefrom. The other ends of these photo receptive light fibers are, similarly, gathered together, and juxtaposed to a photoelectric cell, or other photo sensitive detector.

However, both of these above outlined prior art constructions have the defects of involving a large number of constructional elements, which must be finely adjusted during the manufacture of the apparatus, and, accordingly, of involving high production cost and much labor.

Reference will now be made to a prior art described in an industrial property application assigned to the same assignee as the present application which serves as a point of departure for the present invention. This prior art has been described in Japanese Utility Model Application No. Showa 49-119305 (1974), which has been published in Japan as Japanese Utility Model Laying Open Publication No. Showa 51-118741 (1976), and is entitled "Linear Light Conducting Device". The subject of this prior art related to the field outlined above of film blackened area measuring devices, and, particularly, disclosed a method of constructing simply and cheaply a linear light source and a linear light detector, adapted for mounting on opposite sides of a photographic film which was being moved between them as described above. This prior art film blackening area measuring device will now be explained with respect to FIGS. 1 and 2 of the accompanying drawings.

FIG. 1 is a perspective view of a light conducting rod as used in one embodiment of the device of this previous invention. This light conducting rod, designated by reference numeral 1, is formed of a light transparent material such as plastic, glass, or similar material, which preferably has a high index of refraction, and is generally cylindrical with its ends cut off at right angles, except that a V shaped notch or groove, parallel to the axis of the cylinder, is cut into its side, as seen in FIG. 1. The inner surface of the groove or notch 2 is processed so that it is finely unevenly formed, as by grinding, sandblasting, or the like, so that it diffuses light and is translucent but not transparent. The remainder of the outer surface of the cylindrical rod 1, apart from the groove 2, and also the end surfaces of the rod 1, are all smoothly polished so that they are quite transparent.

In the device of the prior art identified above, two rods such as shown in FIG. 1 are used. At each end of one of these transparent rods there is placed a light source such as a lamp. When these light sources are producing light, therefore, the light enters the ends of the transparent rod, and, in a per se well known fashion, in a manner similar to the process which occurs in well known optical fiber light devices, this light which enters the transparent rod is reflected to and fro along the length of the rod by total internal reflection from the outer cylindrical surface of the rod, which provides light reflection without substantial absorption of the light. For this total internal reflection, it is desirable, as mentioned above, that the refractive index of the material of which the rod is formed should be as high as practicable. Therefore, the light which has entered the transparent rod is, so to speak, trapped within it, and illuminates it along its length. However, when a light ray bouncing about within the transparent rod impinges, not upon the polished smooth cylindrical outer surface of the rod, but upon the surface of the notch or groove, which, as explained above, is not smooth, but is ground to a finely uneven configuration, then total internal reflection may not occur, but, on the contrary, the light beam may escape from the glass rod, or, alternatively, may be deflected at an angle to the axis of the transparent rod so great that total internal reflection does not occur from the next impact of this light beam with the polished smooth outer cylindrical surface of the transparent rod, thus, again, resulting in the escape of the light beam from the transparent rod. Thus, effectively, the transparent rod becomes a linear light emitter, and this light emission occurs not only on the side of the transparent rod on which the groove is formed, but, in fact, also occurs from the other side of the transparent rod as well, by the mechanism explained above. This light diffusion from the uneven surface of the groove occurs all along its length, and is relatively uniform along this length. Thereby, the uneven surface of the groove becomes a linear light emitter of relatively uniform light emitting performance across the width of the film.

Next, according to this prior art construction, if a pair of such light conducting rods 3 and 4 are provided, as shown in FIG. 2, with the V shaped grooves 2 cut in their surfaces being arranged as facing outwards from a piece of developed photographic film 7 which is being passed between these rods, said rods having their axes parallel, and if, as explained above, two light sources 5 are positioned, one at each end of one of these transparent rods 3, so as to illuminate its interior in the above described manner and cause the surface of the groove 2 thereupon to be a linear light source, then, if further two photoelectric detectors 6 such as photo cells are provided at the two ends of the other transparent rod 4, so as to receive light which is picked up by this rod 4 and transmitted along it in the same manner as light is transmitted along the first rod 3, after having passed through the photographic film 7 and after its intensity has been varied according to the amount of development of the photographic film 7, then this second transparent rod 4 will function as a linear light absorber, cooperating with the first light transparent rod 3, which is a linear light emitter, so as to sense the overall amount of development or blackening of the film 7, moment by moment as it passes between the two parallel rods 3 and 4. That is to say, according to the area of blackening of the strip of the photographic film 7 which is between the two rods 3 and 4, the amount of light passing between the two rods 3 and 4 will be reduced, and thereby the output of the two photo cells 6, i.e. their total output, will be reduced. Thus, by integrating the amount of drop of the combined output of the two photo cells 6, compared to their output when the film 7 is substantially transparent, with respect to an integration variable which corresponds to the amount of film 7 passed between the light rods (which may be the same as time, if the film transport speed is constant), then the final result will represent the total area of blackening of the total amount of film developed, and this may be used by a suitable calculating means for determining when to replenish or replace the developer, and how much additional fluid to supply when such replenishment is performed. Thus, an automatic developer replenishment mechanism for an automatic film developing machine may be realised.

In practice, using such a setup, satisfactory practical results have been attained, and automatic control of addition of developer solution to a developing tank has been practically realised. However, in the above explained concept of operation of the above identified prior art, it has been assumed that the light emitting characteristics of the transparent rod 3, with two light sources 5 placed one at each of its ends, and also the light absorbing characteristics of the light receiving transparent rod 4, with photo cells 6 placed at both of its ends, are uniform along the entire lengths of these rods, i.e. across the entire width of the developed film 7. There is a severe disadvantage with regard to this construction, in that, although, if the light outputs of the light sources 5 are arranged so as to be substantially equal and also the light sensitivities of the light sensitive devices 6 are arranged so as to be substantially equal, then such a desirable uniformity over the width of the film of response to blackening of an area of the film is indeed substantially reached; however, if either the light outputs of the light emitting devices 5 or the light sensitivities of the light sensitive devices 6 become unequal, or unbalanced, or are not properly balanced during installation, then the response of the device as a whole to a blackened area on the film will no longer be independent of the position of the blackened area across the width of the film, but will vary according to the position of the image on the film. This is a severe disadvantage, and entails, accordingly, much care during the production of the automatic film developing apparatus, and also frequent checking of the apparatus during use to ensure that the light emitting characteristics of the light emitting sources and the light absorbing characteristics of the light sensitive sources remain equal, and have not altered during use through aging or the like. This, accordingly, entails high cost and expenditure of labor.

SUMMARY OF THE INVENTION

The present invention takes its point of departure from the above identified prior art, and an object of the present invention is to eliminate the above mentioned disadvantage with regard to the necessity for setting the light outputs of the light emitting devices and the photoelectric characteristics of the photo sensitive devices to be equal.

A further object of the present invention is to produce a photographic film blackening area measuring device which is simpler and cheaper to manufacture than the above explained prior art device, and is easier to use and requires less adjustment during use.

Therefore, the present invention proposes in a novel way the omission of one of the light emitting elements and of one of the light absorbing elements in the structure according to the above identified prior art. The remaining light emission device and the remaining light absorption device are arranged so that they are at ends of their respective transparent rods which are opposite.

According to this principle of construction, the present invention provides, in an automatic photographic film development device in which a developed photographic film is moved along a transport path, a photographic film blackening area measuring device, comprising: (a) two rod shaped light conducting members formed of transparent material, the longitudinal surface of each of which is smooth except for a roughened portion elongated parallel to the axis of said rod shaped light conducting member, said rod shaped light conducting members being arranged parallel to one another on opposite sides of the developed photographic film transport path; (b) a single light emitting device, disposed proximate to a first end of a first one of said rod shaped light conducting members, so as to illuminate said first rod shaped light conducting member, substantially no other light source being disposed so as to illuminate said first rod shaped light conducting member; and (c) a single light sensitive device, disposed proximate to a first end of the other rod shaped light conducting member, said first end of said other light conducting member being the most distant end thereof from said first end of said first rod shaped light conducting member, and said light sensitive element being arranged so as to be able to receive light radiated from said first end of said other rod shaped light conducting member, no other light sensitive element being arranged so as to receive light from said other rod shaped light conducting member.

Thus, according to the above construction, the symmetrical arrangement with regard to the left and right hand edges of the moving photographic film which was present in the above identified prior art is replaced by an asymmetrical arrangement of one light emitting device on the one side of the film, approximately opposite its one edge, and one light sensitive device on the other side of the film, approximately opposite its other edge. Although, at first sight, this introduced asymmetry would appear to imply that the device would have an asymmetrical response to blackened areas on the film, according as they are biased towards the left or the right hand edge of the film, in fact, as will be explained later, this is not the case, and accordingly a very useful advantage in simplicity and ease of operation is attained over the above explained prior art device.

BRIEF DESCRIPTION OF THE DRAWINGS

The present invention will become more fully understood from the following description of some preferred embodiments thereof, which is to be taken in conjunction with the accompanying drawings. It should be clearly understood, however, that the description of the embodiments, and the drawings, are all of them provided purely for the purposes of illustration and exemplification only, and are in no way to be taken as limitative of the scope of the present invention. In the drawings.

DESCRIPTION OF THE PREFERRED EMBODIMENT

Figure 3:
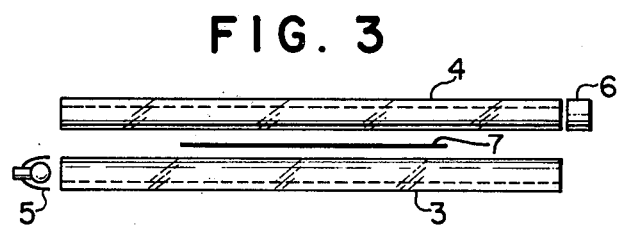
FIG. 3 is a view similar to FIG. 2, relating to a first preferred embodiment of the present invention, and is a schematic cross sectional view through the central axes of the two transparent rods of a photographic film blackening area measuring device according to the present invention, and through a film whose area of blackening is being measured thereby.

The present invention will now be described in detail, with reference to a particular preferred embodiment thereof, which is illustrated in FIG. 3.

Figure 1:
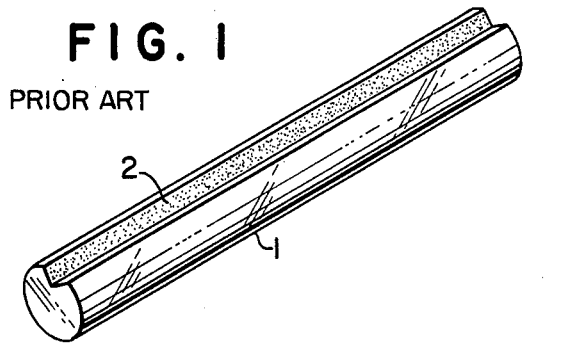
FIG. 1 is a perspective view of a transparent rod with a frosted slot in its side along its axis, as applied to a prior art, and also to the present invention.
Figure 2:
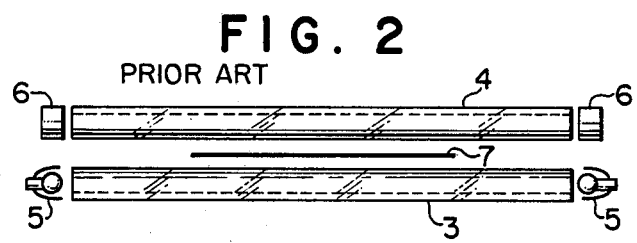
FIG. 2 is a schematic cross sectional view through the central axes of the two transparent rods of a conventional photographic film blackening area detection device, and through a film whose area of blackening is being measured thereby, showing the general construction thereof.

According to a structure broadly similar to the structure shown in FIG. 2, which refers to the above identified prior art, two transparent rods 3 and 4 are arranged parallel to one another, one on each side of a piece of photographic film (not shown) which has been developed and which is being moved between the rods, in order that the area of blackening on this photographic film may be measured. On each of these transparent rods 3 and 4 there is provided a groove, as above explained, and these grooves, in this preferred embodiment, are on the outside of the transparent rod 3 and 4, facing away from the moving film; although, in another embodiment, it would be possible for them to be on the inside, facing towards the film. As in the above described prior art, the lower transparent rod 3 in the drawing is illuminated so that the roughened surface of the groove on it emits light in a linear fashion, and, similarly, the upper transparent rod 4 in the drawing acts as a linear light receptor, by light which passes into it through its smooth surface being scattered by the roughened surface of the groove 2 and thereafter reflected along the rod by a process of total internal reflection until it emerges from one of its ends. According, however, to the particular concept of the present invention, the lower or light emitting transparent rod 3 is illuminated only by one light emitting device 5, which is placed at its left hand end in the drawing. Similarly, again according to the particular concept of the present invention, the upper transparent rod 4, which is receiving light transmitted through the moving photographic film from the lower transparent rod 3, has at its right hand end in the drawing, i.e. at its opposite end from the end of the light emitting transparent rod 3 which is provided with the light emitting device 5, a light sensitive device or photo cell 6. Further, effectively no other illumination is provided for the lower or light emitting rod 3, while no illumination other than that transmitted through the film is allowed to impinge on the upper or light receiving transparent rod 4. Thereby, an asymmetrical device is produced, which might at first appear to produce an asymmetrical output, according to the position of a blackened area upon the film whose blackening area is required to be measured.

Figure 4:
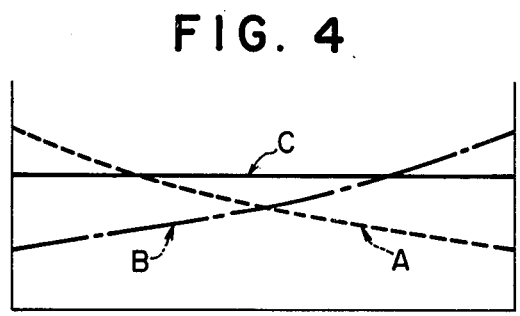
FIG. 4 is a graph showing lines which are, respectively, a representation of the light emitting performance of the light emitting transparent rod in the present invention, a representation of the light sensitivity performance of the light receiving transparent rod and a light sensitive element, in the present invention, and a representation of the overall light transfer performance between a light source and a light sensitive element, in the present invention, all of these being shown with light intensity as the ordinate and distance along the glass rod as the abscissa.

However, in fact, the amount of light emitted by the first transparent rod 4, with respect to distance along its axis, is approximately as shown in FIG. 4 by the dashed line A. That is to say, the intensity of the illumination radiated from the roughened surface of the groove 2 in the rod 3 is greatest at its end nearest to the light emitting device 5, and decreases along the length of the rod to a lower amount near its other end. Further, the light sensitivity characteristic of the assembly of the second transparent light absorbing rod 4 and the photoelectric device 6 are as shown in FIG. 4, approximately, by the chain line B; that is to say, the amount of output of the photoelectric device 6 produced by a given amount of light shining upon a portion of the transparent rod 6, with reference to the distance of said portion along the axis of the transparent rod 6, shows a characteristic such as illustrated by the chain line B; in other words, the photoelectric device 6 produces its greatest output for a particular given quantity of light when that quantity of light is shone on the portion of the transparent rod 4 which is closest to the photoelectric device 6, and the response of the photoelectric device 6 diminishes, the further away from it is the portion of the transparent rod 4 upon which this given quantity of light is directed. In other words, taking these two characteristics together, substantial symmetry in the resultant performance is attained.

That is to say, near the left hand end in the drawing of the rods, where the intensity of illumination of the light emitting transparent rod 3 from the light emitting device 5 is high, the effective sensitivity of the photo cell 6 to this transmitted light is low, because the distance to this photocell 6 is large; and, conversely, at the right hand end in the drawings of the rods, where the distance from the light emitting device 5 is high, and accordingly the amount of light emitted from the light emitting transparent rod 3 is low, the effective sensitivity of the photo sensitive device 6 to this low amount of light is high, because the distance thereto is low. As a combined result of this, as shown by the solid line C in FIG. 4, a substantially uniform combined characteristic is obtained along the entire lengths of the rods 3 and 4; i.e., the diminution in output of the photoelectric device 6, due to a particular amount of blackening on the film passing between the two transparent rods 3 and 4, is substantially independent of the actual position on the film, with respect to its edges, of this blackened area. In fact, as may be inferred from the lines A and B in FIG. 4, a slight diminution of response may occur towards the central portion of the photographic film, but such a diminution is quite unimportant in practical application.

Therefore, when the device as explained above is applied to an automatic film blackening area measuring device for an automatic film developing machine, the position of any blackened areas upon a photographic film which has been developed will not substantially affect the measurement of such blackening area. Also, the measurement of blackening area of the photographic film will not be substantially affected by movements of the processed film as a whole to the left or right as it passes along the film processing path; it should be understood that the film may in practice not extend for the full length of the rods 3 and 4. Thereby, it is possible to obtain a substantially uniform and accurate value corresponding to the total amount of development that has been performed by the developer currently in the developing tank, by a process of integration similar to that explained above with reference to the above identified prior art.

Further, since in the device of the present invention as explained above it is only required to provide one light emitting device and one light sensitive device, no problem arises as to the balancing of the outputs of two such light emitting devices or two such light sensitive devices. Thereby, construction of the device is made easier and cheaper, utilisation of raw materials in the device is reduced, and maintenance of the device is substantially simplified and made more easy and cheap. By this, extremely efficient operation of the device may be attained.

Although in the above shown embodiment the polished surfaces of the transparent rods 3 and 4 are shown as interrupted by roughened grooves 2, in another embodiment this function could be equally served by a mere roughened area on the cylindrical outer surface of the rods within any actual groove being formed therein. Further, although in the shown embodiment these grooves are shown as facing outwards away from the developed film, in another embodiment they could face inwards, although the outward facing construction is preferred.

Throughout the foregoing explanation the terms "blackening" and "blackened area" have been freely used, as terms of art, to denote changes in light transmittive quality of the film caused by its development. However, although these terms are most appropriate to the case of black and white film, they should not be considered as limited to this case. It is quite within the scope of the present invention to use it in connection with a developed color film, and in this case of course the film will not actually be blackened, but rather the translucency of the film with respect to certain wavelengths only of light will be reduced. Thus, the term "blackening" has been used, throughout this specification, solely to indicate reduction of translucency of a developed photographic film, in the widest sense.

Although the present invention has been shown and described in terms of several preferred embodiments thereof, and in language more or less specific with regard to structural features thereof, and with reference to the illustrative drawings, it should be understood that in any embodiment of the present invention various changes, modifications, and omissions of the form and the detail thereof can be made by a person skilled in the art, without departing from the essential scope of the invention. Therefore, it is expressly desired that the scope of the present invention should be uniquely delimited by the legitimate and valid scope of the appended claims, which follow, and not by any of the perhaps purely fortuitous details of the shown embodiments, or of the drawings.

We claim:

1. In an automatic photographic film development device in which a developed photographic film is moved along a transport path,
   a photographic film blackening area measuring device, comprising:
   (a) two rod shaped light conducting members formed of transparent material, the longitudinal surface of each of which is smooth except for a roughened portion elongated parallel to the axis of said rod shaped light conducting member, said rod shaped light conducting members being arranged parallel to one another on opposite sides of the developed photographic film transport path;
   (b) a single light emitting device, disposed proximate to a first end of a first one of said rod shaped light conducting members, so as to illuminate said first rod shaped light conducting member, substantially no other light source being disposed so as to illuminate said first rod shaped light conducting member; and
   (c) a single light sensitive device, disposed proximate to a first end of the other rod shaped light conducting member, said first end of said other light conducting member being the most distant end thereof from said first end of said first rod shaped light conducting member, and said light sensitive element being arranged so as to be able to receive light from said first end of said other rod shaped light conducting member, no other light sensitive element being arranged so as to receive light from said other rod shaped light conducting member.

2. A photographic film blackening area measuring device as defined in claim 1, in which said two rod shaped light conducting members are formed as cylinders with smooth outer cylindrical surfaces and V shaped notches with roughened sides formed in said outer cylindrical surfaces.

3. A photographic film blackening area measuring device according to claim 2, in which said V shaped notches are arranged on the sides of said rod shaped light conducting members remote from the photographic film transport path.

4. A photographic film blackening area measuring device according to claim 2, in which said V shaped notches are arranged on the sides of said rod shaped light conducting members close to the photographic film transport path.

5. A photographic film blackening area measuring device according to claim 1, in which said rod shaped light conducting members are cylindrical rods, part of the outer surfaces thereof extending along their axes being roughened.

* * * * *